United States Patent [19]

Freidinger et al.

[11] Patent Number: 5,189,050

[45] Date of Patent: Feb. 23, 1993

[54] FERMENTATION ANALOGS OF VIRGINIAMYCIN M₁ TO TREAT PANIC AND ANXIETY DISORDER

[75] Inventors: Roger M. Freidinger, Landsale; Mark G. Bock, Hatfield, both of Pa.; Yiu-Kuen T. Lam, Plainsboro, N.J.; Raymond S. Chang, Lansdale, Pa.; Otto D. Hensens, Red Bank, N.J.; Cheryl D. Schwartz, Westfield, N.J.; Deborah L. Zink, Manalapan, N.J.

[73] Assignee: Merck & Co., Inc., Rahway, N.J.

[21] Appl. No.: 709,676

[22] Filed: Jun. 3, 1991

[51] Int. Cl.⁵ .................................. A61K 31/42
[52] U.S. Cl. .................................. 514/375
[58] Field of Search .................................. 514/375

[56] References Cited

U.S. PATENT DOCUMENTS

| 4,762,923 | 8/1988 | Lam et al. | 540/455 |
| 4,772,595 | 9/1988 | Lam et al. | 514/183 |
| 4,820,834 | 4/1989 | Evans et al. | 514/183 |
| 4,859,690 | 8/1989 | Lam et al. | 514/375 |

FOREIGN PATENT DOCUMENTS 411688 2/1991 European Pat. Off. .
90/11773 4/1989 World Int. Prop. O. .

OTHER PUBLICATIONS

Bradwejn, et al., *Enhanced Sensitivity to Cholecystokinin Tetrapeptide in Panic Disorder*, Soc. Neurosci. Abstr. 14(1), p. 291, (1988).
de Montigny, *Cholecystokinin Tetrapeptide Induces Panic Attacks in Healthy Volunteers*, Soc. Neurosci. Abstr. 14(1), p. 291, (1988).
Breadwejn, et al., *Benzodiazepines Antagonize Cholecystokinin-Induced Activation of Rat Hippocampal*, Nature 312, p. 22, (1984).
de Montigny, *Cholecystokinin Tetrapeptide Induces Panic-like Attacks in Healthy Volunteers*, Arch. Gen. Psychiatry, 46, (1989).
Dourish, et al., *Morphine Induced Analgesia in the Rat Paw Pressure Test is Blocked by CCK and Enhanced by the CCK Antagonist MK-329*, Eur. Jour. Pharm. 147, No. 3, pp. 469-472, (1988).
Bouthillier, et al., *Long-term Benzodiazepine Treatment Reduces Neuronal Responsiveness to Cholecystokinin: an Electrophysiological Study in the Rat*, Eur. Jour. Pharm. 151, No. 1, pp. 135-138, (1988).
U.S. Serial No. 07/852,478, Freidinger et al., filed Mar. 12, 1992.

*Primary Examiner*—S. J. Friedman
*Attorney, Agent, or Firm*—Mark R. Daniel; Joseph F. DiPrima

[57] ABSTRACT

Pharmaceutical compositions containing Virginiamycin M₁ having the Formula:

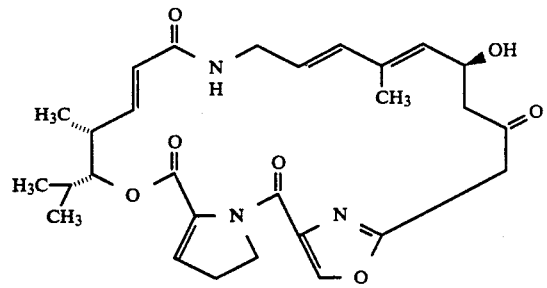

and Virginiamycin M₁ analogs having the Formulae I-IV:

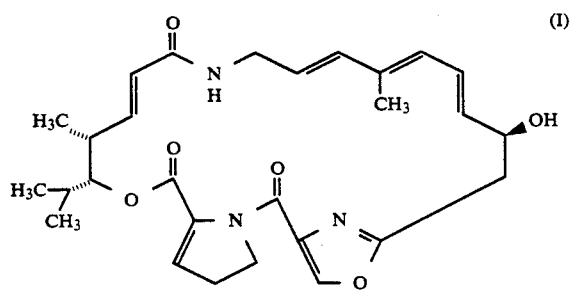

(I)

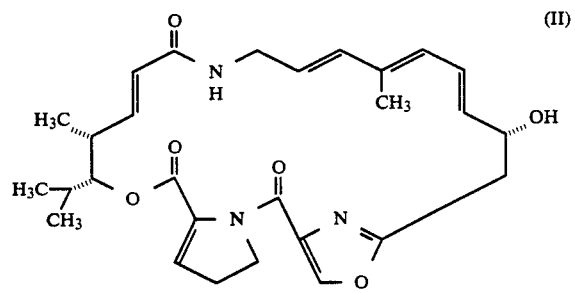

(II)

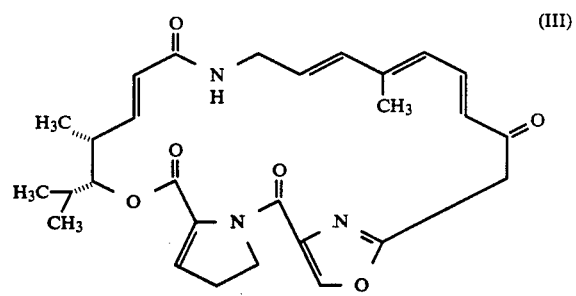

(III)

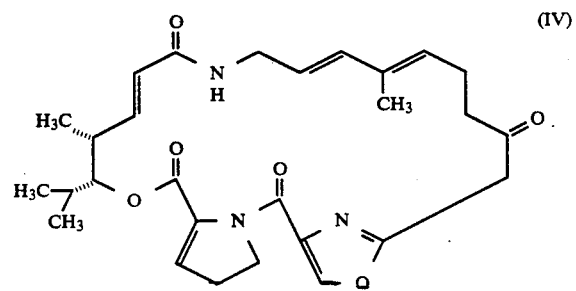

(IV)

are disclosed which are useful in the treatment of panic disorder or anxiety disorder.

15 Claims, No Drawings

FERMENTATION ANALOGS OF VIRGINIAMYCIN M₁ TO TREAT PANIC AND ANXIETY DISORDER

BACKGROUND OF THE INVENTION

This application is related to Merck U.S. Pat. Nos. 4,762,923, 4,772,595 and 4,859,690.

Cholecystokinin (CCK) and gastrin (G) are regulatory peptides which are found in gastrointestinal tissue and in the central nervous system, Mutt, *Gastrointestinal Hormones*, Glass, Ed. Raven Press, N.Y., p. 169 (1980). The isolation of the 33-amino acid polypeptide, cholecystokinin (CCK-33), from porcine intestine, Mutt, V. et al., "Structure of Porcine Cholecystokininpancreozymin. 1. Cleavage with Thrombin and Trypsin", *European J. Biochem.* 6, 156, (1968), was followed by the discovery that it occurs in numerous molecular forms at various sites throughout the peripheral and central nervous systems, Larsson, L. et al., "Localization and Molecular Heterogeneity of Cholecystokinin in the Central and Peripheral Nervous System", *Brain Res.*, 165, 201 (1979). In the mammalian brain the predominant fragments are the carboxy terminal octapeptide, H-Asp-Tyr(SO$_3$H)-Met-Gly-Trp-Met-Asp-Phe-NH$_2$ (CCK-8s, CCK$_{26-33}$) and tetrapeptide, CCK-4 (CCK$_{30-33}$).

The carboxy terminal octapeptide possesses the full biological profile of CCK, Dockray, G. J. et al., "Isolation, Structure and Biological Activity of Two Cholecystokinin Octapeptides from Sheep Brain", *Nature* 274, 711 (1978), and meets many anatomical and biochemical criteria which characterize a neurotransmitter, Vanderhaeghen, J. J. et al., "J. Neuronal Cholecystokinin", *Ann. N.Y. Acad. Sci.*, 448, (1985). The presence of high concentrations of CCK-8s in the mammalian CNS is complemented with findings of specific and high affinity membrane-bound CCK binding sites, Innis, R. B. et al., "Distinct Cholecystokinin Receptors in Brain and Pancreas", *Proc. Natl. Acad. Sci. U.S.A.*, 77, 6917 (1980).

Evidence that more than one form of CCK receptor might exist was first provided in 1980 by Innis and Snyder, Innis, R. B. et al., "Distinct Cholecystokinin Receptors in Brain and Pancreas", *Proc. Natl. Acad. Sci. U.S.A.*, 77, 6917 (1980). At present, CCK receptors have been differentiated into primarily two subtypes based on their affinity for CCK fragments and analogues, Innis, R. B. et al., "Distinct Cholecystokinin Receptors in Brain and Pancreas", *Proc. Natl. Acad. Sci. U.S.A.*, 77, 6917 (1980). The subsequent development of agents which discriminate between different CCK receptor types afforded further support for these assignments, Chang, R. S. L. et al., "Biochemical and Pharmacological Characterization of an Extremely Potent and Selective Nonpeptide Cholecystokinin Antagonist", *Proc. Natl. Acad. Sci. U.S.A.*, 83, 4923 (1986).

The CCK-A receptors, previously known as peripheral CCK receptors, are located in organs such as the pancreas, gallbladder, and colon. They exhibit high affinity for CCK-8s and a lower affinity for the corresponding desulphated fragment, CCK-8d, for CCK-4, and gastrin. Recent autoradiographic results have localized CCK-A receptors in the brain as well, Hill, D. R. et al., "Autoradiographic Localization and Biochemical Characterization of Peripheral Type CCK Receptors in Rat CNS Using Highly Selective Nonpeptide CCK Antagonists", *J. Neurosci.*, 7, 2967 (1987).

The majority of the CCK receptors in the brain are of the CCK-B type. These were previously designated as central CCK receptors. CCK-B receptors are widely distributed throughout the brain and display high affinity for CCK-8s, CCK-4, and pentagastrin, Hill, D. R. et al., "Autoradiographic Localization and Biochemical Characterization of Peripheral Type CCK Receptors in Rat CNS Using Highly Selective Nonpeptide CCK Antagonists", *J. Neurosci.*, 7, 2967 (1987).

In addition to the above mentioned CCK receptor subtypes is a third type, the stomach gastrin receptor, which appears to be closely related to the CCK-B receptor subtype, Beinfeld, M. C., "Cholecystokinin in the Central Nervous System; a Minireview", *Neuropeptides*, 3, 4111 (1983). The minimum fully potent CCK sequence at this receptor is CCK-4, Gregory, R. A., "A Review of some Recent Development in the Chemistry of the Gastrins", *Biorg. Chem.*, 8,497 (1975).

A wide range of physiological responses has been attributed to CCK. In an effort to elucidate its biological roles, researchers have relied primarily on a collection of CCK-A antagonists which has been steadily supplemented and improved to now include very selective, high-affinity agents, Evans, B. E., "Recent Developments in Cholecystokinin Antagonist Research," *Drugs Future*, 14, 971 (1989). In addition to their value as investigative tools, CCK antagonists retain considerable therapeutic potential, Gertz, B. J., "Potential Clinical Applications, of a CCK Antagonist in Cholecystokinin Antagonists," Alan R. Liss, Inc.: New York, pp. 327 (1988).

In recent years, interest in agonists and antagonists of CCK has been stimulated by the possible clinical application of such compounds, Silverman, M. A. et al., "Cholecystokinin Receptor Antagonists, a Review", *Am. J. Gastroenterol*, 82, 703, (1987). The discovery of the presence of CCK in the brain and its significance in relation to its modulation of dopaminergic functions, effects on satiety, its roles in nociception, in anxiety, and other brain functions, Vanderhaeghen, J. J., et al., "Neuronal Cholecystokinin", *Ann. N.Y. Acad. Sci.* 448 (1985) has understandably intensified the search for CCK-B selective agents. Since the relevant biologically active fragment, CCK-8s, has a half-life of less than 1 hour, Deschodt-Lanckman, K., et al., "Degradation of Cholecystokinin-like Peptides by a Crude Rat Brain Synaptosomal Fraction: a Study by High Pressure Liquid Chromatography", *Reg. Pept.*, 2, 15 (1981), implicit in the development of candidates for clinical use are criteria of high potency, selectivity, long in-vivo duration, oral bioavailability, and capability of penetrating the blood-brain barrier. These are strict prerequisites, given the tenous stature of peptides as drugs, Veber, D. F., et al., "The Design of Metabolically-stable Peptide Analogs", *Trends Neurosci.* 8, 392 (1985).

Nevertheless, by employing stratagems which stabilize peptide structures, advances have been made toward developing highly potent and selective peptidal CCK-B receptor ligands Charpentier, B. et al., "Cyclic Cholecystokinin Analogues with High Selectivity for Central Receptors". *Proc. Natl. Acad. Sci. U.S.A.*, 85, 1968, (1988). Analogues are now available which have proven resistant to enzymatic degradation Charpentier, B. et al., "Enzyme-resistant CCK Analogs with High Affinities for Central Receptors", *Peptides*, 9 835 (1988). Despite favorable receptor binding profiles, this class of compounds fails to meet previously cited key requirements which characterize a drug candidate. In response, researchers have turned to non-peptide compounds which offer a broader range of structure and physico-chemical properties.

Antibiotics of the Virginiamycin family have been used as food additives to improve the growth of poultry, swine and cattle. Although growth promotion by antibiotics is not thoroughly understood, there is little doubt that the effect is due in part to an inhibition of the intestinal flora, Coccito, Micro. Rev. 43: 145 (1979). Virginiamycin $M_1$ and related antibiotics are generally specific for gram-positive bacteria and prevent cell multiplication. The virginiamycin antibiotics are most effective when in their complex form, that is when they are composed of both M and S components, Coccito, Micro. Rev. 43: 145 (1979). The wide use of these antibiotics as growth promoters relates their low toxicity, lack of accumulation in animal tissues, no production of resistant mutants and a rapid degradation in animal feces.

It is, therefore, an object of this invention to prepare pharmaceutical compostions containing the compounds of this invention for use in the treatment of panic disorder or anxiety disorder in a mammal, especially a human. The compositions of this invention are also useful in the treatment of oncologic disorders, controlling pupil constriction in the eye, or treating a withdrawal response produced by chronic treatment or abuse of drugs or alcohol.

SUMMARY OF THE INVENTION

Pharmaceutical compositions containing Virginiamycin $M_1$ having the Formula:

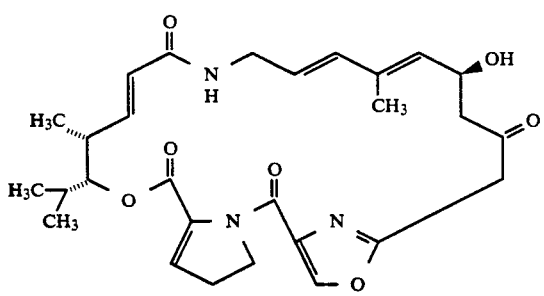

and Virginiamycin $M_1$ analogs having the Formulae I-IV:

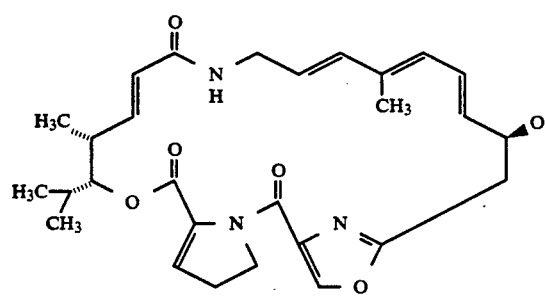
(I)

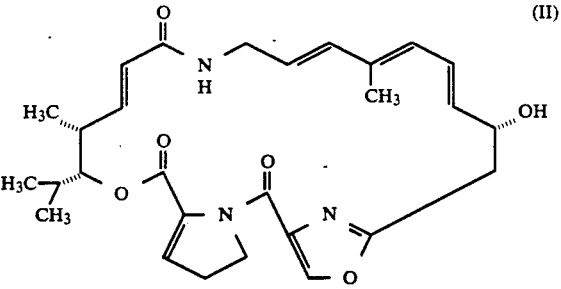
(II)

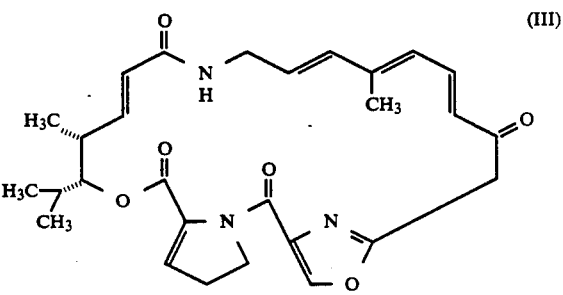
(III)

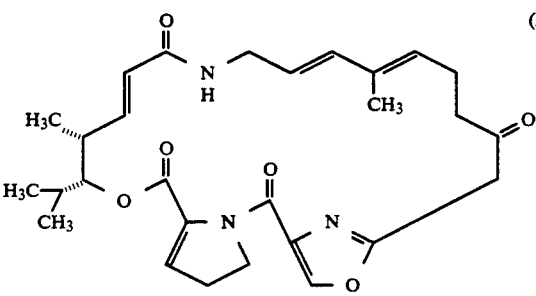
(IV)

are useful in the treatment of panic disorder and anxiety disorder in a mammal, especially a human. The compositions of this invention are also useful in the treatment of oncologic disorders, controlling pupil constriction in the eye, or treating a withdrawal response produced by chronic treatment or abuse of drugs or alcohol.

DETAILED DESCRIPTION OF THE INVENTION

The pharmaceutical compositions of this invention contain Virginiamycin $M_1$ having the formula:

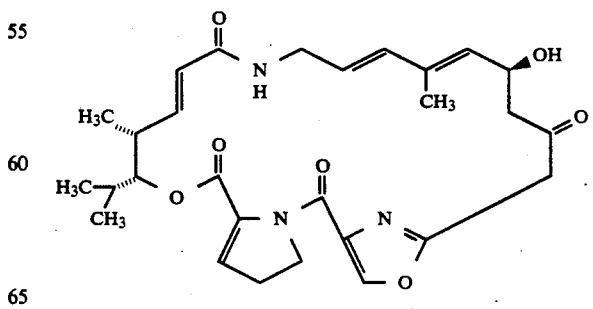

and pharmaceutical compositions containing Virginiamycin $M_1$ analogs having the Formulae I-IV:

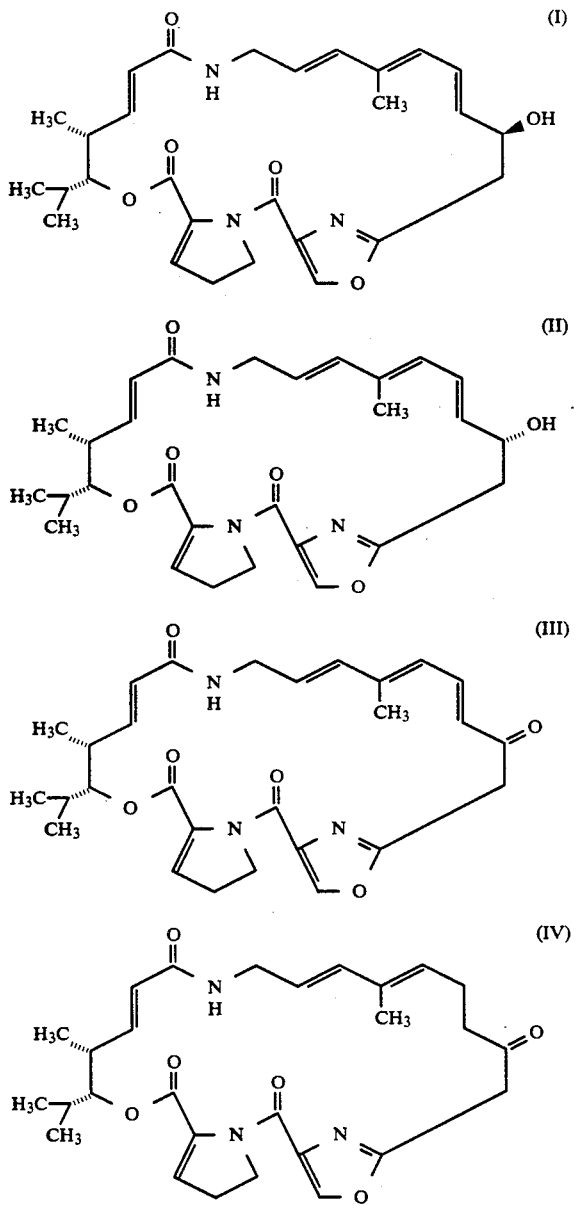

Pharmaceutical compositions containing Virginiamycin M₁ and the compounds of Formulae I, III and IV are produced by controlled aerobic fermentation of a strain of the *Streptomyces olivaceus*. It is to be understood that for the fermentation production of virginiamycin M₁ and the compounds of Formulae I, III and IV the present invention is not limited to the use of this specific species or strain of Streptomyces. It is especially desired and intended that there be included within the scope of this invention, the use of other natural or artificial mutants produced or derived from the described cultures, or other variants or species of the genus Streptomyces in so far as they can produce virginiamycin M₁ and the compounds of Formulae I, III and IV or any related analogs. The artificial production of mutant species or strains of this strain of Streptomyces may be achieved by conventional physical or chemical mutagens, for example, ultraviolet irradiation of the described cultures, or nitrosoguanidine treatment and the like. Recent recombinant DNA techniques such as plasmid incorporation in bacteria and fungi and the like may also prove useful.

Virginiamycin M₁ and the compounds of Formulae I, III and IV are produced by the controlled aerobic fermentation of a species of Streptomyces which has been deposited in the American Type Culture Collection, 12301 Parklawn Drive, Rockville, Md. 20852, U.S.A., on Jul. 29, 1986, under the "Budapest Treaty on the International Recognition of the Deposit of Microorganisms for the Purposes of Patent Procedure" and has been assigned ATCC number 53527.

The Streptomyces species was isolated from soil associated with tree roots in Pimpri, India and expresses morphological and cultural characteristics as shown in the following table:

TABLE I

| | |
|---|---|
| Morophology: | Sporophores form very loose coils, chains are more than 15 spores in length, spores are spherical to oval, and are about 0.9 m to 0.9 × 1.2 m in size |
| Cultural Characteristics: | Yeast extract-malt extract agar |
| (ISP Medium 2) | |
| V: | Reverse - grayish brown edged with gray |
| A: | Light gray mixed with white and edged with dark gray |
| SP: | None |
| Oatmeal agar (ISP Medium 3) | |
| V: | Reverse - light grayish tan edged with gray |
| A: | Light gray mixed with white, edged with dark gray |
| SP: | None |
| Inorganic salts-starch agar (ISP Medium 4) | |
| V: | Reverse - grayish tan edged with gray |
| A: | Light gray mixed with white, edged with dark gray |
| SP: | None |
| Glycerol asparagine agar (ISP Medium 5) | |
| V: | Reverse - tan edged with gray |
| A: | Light gray and white edged with light gray |
| SP: | None |
| Peptone-iron-yeast extract agar (ISP Medium 6) | |
| V: | Reverse - tan |
| A: | Pale gray mixed with white and edged with medium gray |
| SP: | None |
| Melanin: | None |
| Tyrosine Agar (ISP Medium 7) | |
| V: | Reverse - tan edged with brown |
| A: | Mixed grayish - white and gray edged with dark gray |
| SP: | Slight browning of medium |
| Czapek-Dox Agar | |
| V: | Reverse - grayish tan |
| A: | Light gray mixed with white |
| SP: | Slight browning of medium |

V = vegetative growth;
A = aerial mycelium;
SP = soluble pigment
Color number designations taken from Color Harmony Manual, 1958, 4th Edition, Container Corporation of America, Chicago, Illinois.

The carbon utilization of ATCC 53527 was determined using Pridham-Gottlieb basal medium (ISP Medium 9) supplemental with 1% carbon sources as seen in the following table:

TABLE II

| | | | |
|---|---|---|---|
| Glucose | + | Mannitol | + |
| Arabinose | + | Mannose | + |
| Cellulose | − | Raffinose | ± |
| Fructose | + | Rhamnose | + |
| Inositol | + | Sucrose | + |
| Lactose | + | Xylose | + |

TABLE II-continued

| | |
|---|---|
| Maltose | + |

[+ = growth;
± = growth poor or questionable;
− = no growth as compared to negative control (no carbon source)]

The temperature growth range and oxygen requirements were determined using yeast extract-dextrose+-salts agar. The results are shown in the following table:

TABLE III

Temperature range (Yeast extract-dextrose + salts agar)
| | |
|---|---|
| 28° C.— | Good vegetative growth and sporulation |
| 37° C.— | Good vegetative growth and sporulation |
| 42° C.— | No growth |
| 50° C.— | No growth |

Oxygen requirements (Stab culture in yeast extract-dextrose + salts agar)

Aerobic

All readings taken after three weeks at 28° C. unless noted otherwise. The pH of all media is approximately neutral (6.8–7.2).

Aerobic

All readings taken after three weeks at 28° C. unless noted otherwise. The pH of all media is approximately neutral (6.8–7.2).

The cultural characteristics of this organism are compared with culture descriptions of Streptomyces species described in Berger's Manual of Determinative Bacteriology, Eighth Edition, 1974, Williams & Wilkens, Baltimore, Md., and the Streptomeyces species is presumptively identified as a strain of *Streptomyces olivaceus*. Furthermore, a direct comparison of this organism with the designated strain of *Streptomyces olivaceus* (ATCC 3335) was made. Although some subtle differences were observed in the coloration of the aerial and vegetative growth of these strains, they were found to be identical in micromorphology and carbon utilization patterns. This organism is therefore considered a strain of *Streptomyces olivaceus*.

The fermentation is carried out at a temperature range of from about 20° C. to about 37° C., with 28° C. being preferred. Generally, the composition of the assimilable nutrient medium may be varied over a wide range. The essential nutrient ingredients are a carbon source and a nitrogen source. Other essential nutrients are provided via mineral salts such as chlorides, nitrates, sulfates, carbonates and phosphates of sodium, potassium, ammonium and calcium. The nutrient medium may also contain sources of inorganic trace elements such as magnesium, iron, copper, manganese, zinc, cobalt and the like.

Typical sources of carbon include; sugars, oils, organic acids, dextrin, starches, glycerol and the like. Typical nitrogen sources include; amino acids, vegetable meals, and extracts (e.g., malts, soy, cotton seed, figs, tomato, corn, etc.), animal viscera, various hydrolysates (e.g., casein, yeast, etc.) and industrial by-products such as lard water and distillers solubles.

The maximum yield of Virginiamycin $M_1$ and the compounds of Formulae I, III and IV is achieved within about 24 to about 96 hours, usually in about 48 to about 72 hours, of fermentation under optimum conditions. The inoculum for the fermentation is provided from vegetative growth in a medium which supports rapid growth of the microorganism or by direct inoculation of frozen biomass.

The terms "seed" and "production" media are employed as terms of art. Generally, a seed medium supports rapid growth of the microorganism and an aliquot (seed) of this medium is used to inoculate a production medium for a large scale fermentation.

Following fermentation, the accumulated virginiamycin $M_1$ and the compounds of Formulae I, III and IV are recovered from the culture broth by conventional chromatographic means. The individual compounds are separated by reverse phase high performance chromatography.

Virginiamycin $M_1$ and the compounds of Formulae I, III and IV are isolated from whole fermentation broth by the addition of a nearly equal volume of a moderately polar solvent immiscible in water. Such solvents include chloroform, ethyl acetate, methyl ethyl ketone and the like, with methyl ethyl ketone being preferred. The layers are allowed to settle and the organic layer collected. The organic layer contains virginiamycin $M_1$ and the compounds of Formulae I, III and IV.

Isolation of the various compounds from the fermentation broth is based on specific biological activity. The products resulting from the chemical conversion of virginiamycin $M_1$ to compound III and subsequently to compounds I and II are also assayed for biological activity. The biological assays include gastrin binding to mammalian gastric glands, preferably guinea pig and CCK binding to mammalian brain, preferably guinea pig or mammalian pancreas, preferably rat.

The active organic layer isolated from the culture broth was flash evaporated under reduced pressure at a temperature of about 30° C. to about 50° C., with 40° C. being preferred, and partitioned between a saturated hydrocarbon such as hexane and an alcohol such as methanol. The methanol layer is flash evaporated at about 30° C. to about 50° C., with 40° C. being preferred, under pressure and chromatographed on silica gel using a mobile phase of acetone about 50% to about 75% in hexane. The active fraction was purified by reverse phase high performance liquid chromatography (HPLC).

Virginiamycin $M_1$ is converted to the compound of Formula III by the addition of about 1 mole equivalent of methanesulfonyl chloride to an anhydrous pyridine solution of Virginiamycin $M_1$. The mesylation reaction is allowed to proceed at about 25° C. for about 20 minutes and the pyridine is removed by flash evaporation. The residue is partitioned in about 1% aqueous NaCl and dichloro-methane. The organic layer is then dried and chromatographed by reverse phase HPLC. The compound of Formula III is reduced to the compounds of Formulae II and I by sodium borohydride reduction. To a methanolic solution of the compound of Formula III is added a slight excess of 1 mole equivalent of a NaBH$_4$/methanol solution at about 10 mg/ml. Purification is similar to that for the fermentation products.

Biological activity of Virginiamycin $M_1$ and the compounds of Formulae I, II, III and IV is determined by gastrin receptor binding, pancreas CCK receptor binding, brain CCK binding and microbial growth inhibition assays.

The pharmaceutical compositions containing the compounds of Virginiamycin $M_1$ and Formulae I–IV may further be useful in the treatment or prevention of central nervous system disorders including neurological and pyschiatric disorders. Examples of such central nervous system disorders include anxiety disorder and panic disorder. Additional examples of central nervous system disorders include panic syndrome, anticipatory anxiety, phobic anxiety, panic anxiety, chronic anxiety, and endogenous anxiety.

The pharmaceutical compositions containing the compounds of Virginiamycin $M_1$ and Formulae I-IV may further be useful in the treatment of oncologic disorders. Examples of such oncologic disorders include small cell adenocarcinomas and primary tumors of the central nervous system glial and neuronal cells. Examples of such adenocarcinomas and tumors include, but are not limited to, tumors of the lower esophagus, stomach, intestine, colon and lung, including small cell lung carcinoma.

The pharmaceutical compositions containing the compounds of Virginiamycin $M_1$ and Formulae I-IV may further be used to control pupil constriction in the eye. The compounds may be used for therapeutic purposes during eye examinations and intraocular surgery in order to prevent miosis. The compounds may further be used to inhibit miosis occurring in association with iritis, uveitis and trauma.

The pharmaceutical compositions containing the Virginiamycin M1 and Formulae I-IV compounds of Formula I may further be useful for preventing of treating the withdrawal response produced by chronic treatment or abuse of drugs or alcohol. Such drugs include, but are not limited to cocaine, alcohol or nicotine.

The compounds of the instant invention may be administered to a human subject either alone or, preferably, in combination with pharmaceutically-acceptable carriers or diluents, optionally with known adjuvants, such as alum, in a pharmaceutical composition, according to standard pharmaceutical practice. The compounds can be administered orally or parenterally, including intravenous, intramuscular, intraperitoneal, subcutaneous and topical administration.

For oral use of an antagonist of CCK, according to this invention, the selected compounds may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

When a pharmaceutical compositions containing the Virginiamycin $M_1$ and Formulae I-IV is used as an antagonist of CCK or gastrin in a human subject, the daily dosage will normally be determined by the prescribing physician with the dosage generally varying according to the age, weight, and response of the individual patient, as well as the severity of the patient's symptoms. However, in most instances, an effective daily dosage will be in the range of from about 0.005 mg/kg to about 50 mg/kg of body weight, and preferably, of from about 0.05 mg/kg to about 50 mg/kg of body weight, and most preferably, of from about 0.5 mg/kg to about 20 mg/kg of body weight administered in single or divided doses.

In some cases, however, it may be necessary to use dosage levels outside these limits. For example, doses as low as about 1 ng/kg, about 0.005 $\mu$g to about 0.05 $\mu$g, or about 100 ng to about 100 $\mu$g/kg may be administered.

In the effective treatment of panic syndrome, panic disorder, anxiety disorder and the like, preferably about 0.05 mg/kg to about 0.5 mg/kg of CCK antagonist maybe administered orally (p.o.), administered in single or divided doses per day (b.i.d.). Other routes of administration are also suitable.

The following examples illustrate the present invention without, however, limiting the same thereto.

EXAMPLE 1

Fermentation

A lyophilized tube of the Streptomyces ATCC No. 53527 was added under aseptic conditions to 54 ml of a seed medium in a 250 ml baffled Erlenmeyer flask. The seed media contained the following: dextrose, 1 gm/L; soluble starch, 10 g/L; beef extract, 3 g/L; ardamine pH, 5 g/L; NZ amine, 5 g/L; $MgSO_4'' 7H_2O$, 0.08 g/L; phosphate buffer, 2 ml/L and $CaCO_3$, 0.5 g/L. The pH of the medium was between 7.0 and 7.2. The flask was maintained at 28° C. on a 220 rpm rotary shaker for 48 hours. Ten ml of the 48 hour culture was aseptically transferred to 500 ml in a 2 L baffled flask and incubated at 28° C. on a 220 rpm rotary shaker for 24 hours. A 500 ml inoculum from the second seed culture was added to 10 L of production medium in a 14 L fermenter. The production media contained corn gluten meal, 5.0 g/L; primatone HS, 2.5 g/L; yeast extract (Fidco), 1.0 g/L; malt extract, 10.0 g/L; sucrose, 5.0 g/L; $CaCO_3$, 5.0 g/L and P-2000, 2.0 ml. The pH of the production medium was between 7.2 and 7.4. The inoculated production media was incubated for 64 hours at 28° C., aerated at a flow of 3 L per minute and agitated at 400 rpm.

EXAMPLE 2

Isolation and Characterization of Virginiamycin $M_1$ and Compounds of the Formulae I, III and IV Forty L of whole culture broth from Example 1 was extracted with 48 L of methylethyl ketone. The organic layer contained the biological activity and was flash evaporated under reduced pressure at 40° C. to give a residue. The residue was partitioned between hexane, 1 L, and methanol, 1 L, with the hexane layer being discarded. The active methanol layer was flash evaporated under reduced pressure at 40° C. to yield a 50 g dry weight sample. Flash chromatography of this material in 5 runs on 500 g silica gel 60 (4 mm) using 50% acetone/hexane and then 75% acetone/hexane as the mobile phases yielded active fractions with a total dry weight of 3 grams. Subsequent Preparative reverse phase high performance liquid chromatography of this material in 3 runs on a Zorbax C-8, 2.12×25 cm, column using 40% acetonitrile/water as the isocratic mobile phase at room temperature and 15 ml/min yielded 92 mg of virginiamycin $M_1$; 5.2 mg of the compound of Formula I; 16.4 mg of the compound of Formula III and 25.9 mg of the compound of Formula IV.

Physiochemical characterization of the Virginiamycin $M_1$ isolated from the present fermentation was identified by comparison with EI-MS and $^1$H-NMR data (M+ =525) from the literature, Kingston et al., J. Chem. Soc. 19: 1669-1676 (1966), and an authentic sample obtained by purifying a commercially available Virginiamycin. Subsequent biological/biochemical testing on Virginiamycin $M_1$ was performed on this authentic sample. Both samples showed identical HPLC retention times and UV spectra ($\lambda_{max}$=210.5 nm; E %=535). A 300 MHz $H^1$-$H^1$ homonuclear correlation NMR spectrum was recorded for the first time for characterization.

High resolution mass spectral data of the compound of Formula I revealed a molecular formula of $C_{28}H_{35}N_3O_6$ (calculated: 509.2526; found: 509.2528). Its 300 MHz $H^1$-NMR spectrum, see FIG. 1, in $CD_2Cl_2$ further corroborated the purity and identity of this compound. Broad band decoupled $C^{13}$-NMR spectrum in $CD_2Cl_2$ revealed resonances at 12.11; 18.82; 19.77; 20.34; 29.91; 30.13; 36.77 38.87; 42.26; 51.08; 70.93; 82.46; 123.77; 123.85; 125.78; 126.46; 127.11; 127.72; 129.20; 132.85; 132.93; 135.20; 137.13; 143.29; 143.58; 161.37; 161.86; 167.13 ppm. Its ultraviolet spectrum in methanol displayed absorption maxima at 212 nm (E %=557) and 274.5 nm (E %=764). Its infrared spectrum in $CH_2Cl_2$ solution showed absorption bands at 3595; 3375; 1730; 1670 and 1620 cm$^{-1}$. The natural and semisynthetic compound, Example 4, showed identical mass, $H^1$-NMR, and UV spectra, and HPLC retention time and allowed the assignment of the following structure:

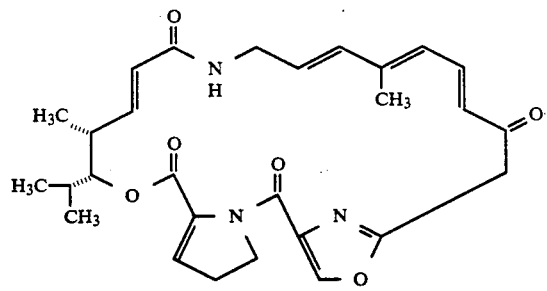

High resolution mass spectral data for the compound of Formula III revealed a molecular formula of $C_{28}H_{33}N_3O_6$ (calculated: 507.2369; found: 507.2369). Its 300 MHz $H^1$-NMR spectrum, see FIG. 3, in $CD_2Cl_2$ further corroborated the purity and identity of this product. Its broad band decoupled $C^{13}$-NMR spectrum in $CD_2Cl_2$ revealed resonances at 12.19; 18.78; 19.60; 21.37; 30.10; 30.22; 37.60; 40.65; 42.04; 52.33; 81.18; 125.38; 126.56; 126.79; 127.25; 129.46; 131.85; 136.98; 142.91; 143.20; 143.32; 146.19; 160.28; 160.54; 167.12; and 192.78 ppm. Its ultraviolet spectrum in methanol displayed absorption maxima at 212 nm (E %=545.5) and 325 nm (E %=417). Its infrared spectrum in $CH_2Cl_2$ solution showed absorption bands at 3380; 1730; 1662 and 1625 cm$^{-1}$. The natural and semisynthetic compound, Example 3, showed identical mass, $H^1$-NMR, and UV spectra, and HPLC retention time and allowed the assignment of the following structure:

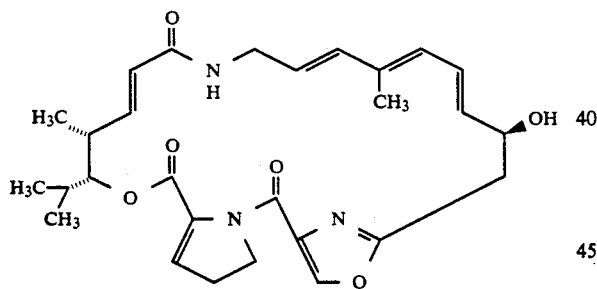

High resolution mass spectral data for the compound of Formula IV on the bis-trimethylsilyl derivative revealed a molecular formula of $C_{28}H_{35}N_3O_6+T_2$ (calculated 653.3316; found: 653.3452). Its 300 MHz H'-NMR spectrum, see FIG. 4, in $CD_2Cl_2$ further corroborated the purity and identity of this product. Its ultraviolet spectrum in methanol is almost identical to that of Virginiamycin $M_1$ and displayed an absorption maximum at 213 nm (E %=542) and allowed the assignment of the following structure:

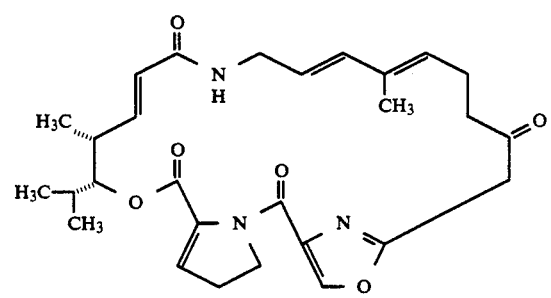

EXAMPLE 3

Synthesis of the Compound of Formula III

Virginiamycin $M_1$, form Example 2 or obtained commercially, was converted to the compound of Formula III by adding methanesulfonyl chloride, 0.2 ml, to 199.36 mg of Virginiamycin $M_1$ in anhydrous pyridine solution, 5 ml. The mesylation reaction was allowed to proceed at room temperature for 20 minutes. Flash evaporation of the solvent, pyridine, under reduced pressure and at 40° C. gave a residue. Partition of this residue in 1% aqueous NaCl, 20 ml, and dichloromethane (2×25 ml) followed by drying the organic layers in anhydrous $Na_2SO_4$ and flash removal of solvent under reduced pressure and at 40° C. yielded 245 mg of a crude product. Analytical high performance liquid chromatography of this product revealed the presence of compound III as the predominant product and the absence of Virginiamycin $M_1$. Preparative reverse phase chromatography of the crude product on a Zorbax ODS column with 40% aqueous MeCN as the mobile phase at 15 ml/minutes provided 88.15 mg of pure compound III.

EXAMPLE 4

Synthesis of Compounds of the Formulae I and II

Compound III was converted to compounds of the Formulae I and II. To a methanolic solution, 10 ml of compound III, from Example 1 or Example 3, was added 0.5 ml of a 10 mg/ml $NaBH_4$/MeOH solution.

High pressure liquid chromatographic analysis of the reaction mixture revealed that the reaction was immediate and the products were compound I and its epimer, compound II. The reaction was then worked up. The addition of acetone, 0.1 ml, to the reaction mixture destroyed any excess reagent. Partition of the mixture between 1% aqueous NaCl, 50 ml, and $CH_2Cl_2$, $2 \times 50$ ml, followed by drying the organic layers in anhydrous $Na_2SO_4$ and flash evaporation under reduced pressure at 30° C. afforded 54.8 mg material. Purification of this material on a preparative Zorbax ODS column, $2.12 \times 25$ cm, with 35% aqueous MeCN as the isocratic mobile phase at 15 ml/min at room temperature yielded 27.69 mg of Compound I and 15.7 mg of its epimer, compound of the Formula II.

The physiochemical characterization of the compound of Formula I is presented in Example 2.

High resolution mass spectral data for the compound of Formula II revealed a molecular formula of $C_{28}H_{35}N_3O_6$ (calculated: 509.2526; found: 509.2528). Its 300 MHz $H^1$-NMR spectrum, see FIG. 2, in $CD_2Cl_2$ further corroborated the purity and identity of this compound. Its broad band decoupled $C^{13}$-NMR spectrum in $CD_2Cl_2$ revealed resonances at 12.03; 18.83; 19.67; 20.47; 30.07; 35.95; 39.10; 42.06; 51.04; 69.88; 81.75; 124.39; 124.47; 125.52; 126.98; 127.51; 127.57; 129.60; 129.62; 132.61; 135.19; 137.19; 143.22; 143.50; 161.23; 161.90 and 167.04 ppm. Its ultraviolet spectrum in methanol displayed absorption maxima at 212 nm (E %=522) and 274.5 nm (E %=701). Its infrared spectrum in $CH_2Cl_2$ solution showed absorption bands at 3600, 3375; 1730; 1670 and 1625 $cm^{-1}$. These characteristics allowed the assignment of the following structure:

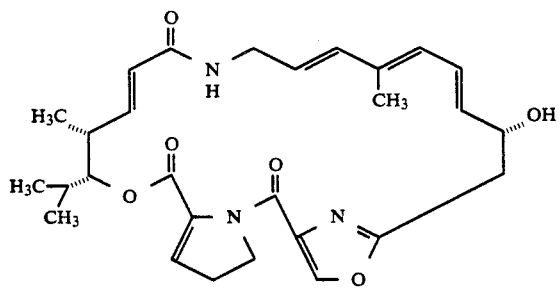

EXAMPLE 5

Gastrin Receptor Binding in Guinea Pig Gastric Glands

Guinea pig gastric mucosal glands were prepared by the procedure of Praissman et al., *J. Receptor Res.* 3:647 (1983). Stomachs from male Hartley guinea pigs (250–400 g body weight) were washed thoroughly and minced with fine scissors in HEPES buffer consisting of the following: 130 mM NaCl, 12 mM $NaHCO_3$, 3 mM $NaH_2PO_4$, 3 mM $Na_2HPO_4$, 3 mM $K_2HPO_4$, 2 mM $MgSO_4$, 1 mM $CaCl_2$, 5 mM glucose and 4 mM L-glutamine, 25 mM HEPES at pH 7.4. The minced tissues were washed and incubated in a 37° C. shaker bath for 40 minutes, with HEPES buffer containing 0.1% collagenase and 0.1% bovine serum albumin (BSA), and bubbled with 95% $O_2$ and 5% $CO_2$. The tissues were passed twice through a 5 ml glass syringe to liberate the gastric glands, and then filtered through 200 mesh nylon. The filtered glands were centrifuged at $270 \times$ g for 5 minutes and washed twice by resuspension and centrifugation.

The washed guinea pig gastric glands were resuspended in 25 ml of HEPES buffer containing 0.25 mg/ml of bacitracin. For binding studies, 14.2 ml of 50% $MeOH/H_2O$ (for total binding) or gastrin (1 mM final concentration, for nonspecific binding) or broth or test compound from Examples 2, 3 or 4 and 20 ml of $^{125}$I-gastrin (New England Nuclear [NEN], 20,000 cpm 20 ml) were added to 220 ml of gastric glands in triplicate tubes which were aerated with 95% $O_2$ and 5% $CO_2$ and capped. The reaction mixtures, after incubation at 25° C. for 30 minutes in a shaking water bath, were filtered under reduced pressure on glass GF/B filters (Whatman) and immediately washed with $3 \times 4$ ml of HEPES buffer containing 0.1% BSA fraction V. The radioactivity on the filters was measured using a Beckman 5500 gamma counter for $^{125}$I-gastrin.

The results of the gastrin binding assay are shown in the following table:

TABLE IV

| Compound | Gastrin Receptor Binding $IC_{50}$ (nM) |
|---|---|
| Virginiamycin $M_1$ | 710 |
| I | 12 |
| II | 13 |
| III | 90 |
| IV | 360 |

EXAMPLE 6

Pancreatic Cholecystokinin Receptor Binding Assay

Radiolabeled CCK-8 was purchased from New England Nuclear as $^{125}$I-CCK-8. Receptor binding was performed according to Innis and Snyder Proc. Natl. Acad. Sci., 77, 6917 (1980), with the minor modification of adding the additional protease inhibitors, phenylmethane sulfonyl fluoride (PMSF) and o-phenanthroline, which have no effect on the $^{125}$I-CCK receptor binding assay. All assays were performed in triplicate. Pancreatic receptor membranes were prepared by homogenzing a gram of fresh rat pancreas tissue in 30 ml TRIS-HCl (50 mM), pH 7.7 using a Brinkman polytron PT10 (Brinkman). The homogenate was washed twice and collected by centrifugation at 48,000 $\times$ g at 4° C. for 10 minutes. The membranes were resuspended in assay buffer consisting of 5 mM dithiothieitol, 0.1 mM bacitiacin, 5 mM $MgCl_2"H_2O$, 0.2% heat denatured BSA, 1.2 mM PMSF and 0.5 mM O-phenanthroline at a concentration of 100 ml per gram of pancreas. To each incubation tube, in an ice-bath, containing 0.45 ml of membrane preparation, 25 ml of assay buffer (for total binding) or unlabeled CCK 26–33 (for non-specific binding) or broth or test compound from Examples 2, 3 or 4 for determining the inhibition of specific CCK binding by broths, and 25 ml of $^{125}$I-CCK were added. The reaction mixtures were mixed briefly and placed in a 37° C. water bath with gentle shaking for 30 minutes. The reaction mixtures were then diluted with 4 ml of ice-cold TRIS buffer, pH 7.7, containing 1 mg/ml bovine serum albumin and immediately filtered in Watman G F/B filters. The filters were washed with $3 \times 4$ ml of the same buffer and the radioactivity associated with the filters was counted in a Beckman 5500 gamma counter. Broths were prepared by adding two volumes of acetone to original broth; supernatants were freeze dried after centrifugation at 1500 g for 10 minutes. The dried samples were then brought up in methanol/H₂O (1:1) and ready for assay.

The results of the pancreatic CCK binding assay are shown in the following table:

TABLE V

Pancreatic CCK Receptor Binding

| Compound | IC$_{50}$ (nM) |
|---|---|
| Virginiamycin M$_1$ | >100,000 |
| I | >10,000 |
| II | >10,000 |
| III | >10,000 |

EXAMPLE 7

Brain Cholecystokinin Receptor Binding Assay

CCK-8 binding was performed according to the description for the pancreatic method, with modifications by Saito et al., J. Neurochem., 37, 483 (1981).

The brains from male Hartley guinea pigs (300–500 g) were removed and placed in ice-cold 50 mM Tris HCl plus 7.58 g/L Trizma-7.4 [pH 7.4 at 25° C.]. The cerebral cortex was dissected and used as a receptor source and each gram of fresh guinea pig brain tissue was homogenized in 10 ml of Tris/Trizma buffer, pH 7.4, with a Brinkmann polytron PT-10. The homogenates were centrifuged at 42,000× g for 15 minutes, then the resulting pellets were resuspended in 200 volumes of binding assay buffer (10 mM N-2-hydroxy-ethyl-piperazine-N'-2-ethane-sulfonic acid (HEPES), pH 7.7 at 25° C., mM MgCl₂, 1 mM ethylene glycol-bis-(β-amino-ethyl-ether-N,N'-tetraacetic acid (EGTA), 0.4% BSA and 0.25 mg/ml bacitracin, pH 6.5).

The remainder of the binding assay method was as described for the pancreatic method, Example 6, except that the reaction mixtures were incubated at 25° C. for 2 hours before filtration and the filters were washed with HEPES buffer.

The results of the brain CCK binding assay are shown in the following table:

TABLE VI

Brain CCK Receptor Binding

| Compound | IC$_{50}$ (nM) |
|---|---|
| Virginiamycin M$_1$ | 571 |
| I | 7.8 |
| II | 6.1 |
| III | 13.3 |
| IV | 270 |

EXAMPLE 8

Antibiotic Activity

The compounds of Formulae I, III, and IV and virginiamycin M₁ from Example 2 were assayed for antibiotic activity following a method described by Matsen and Barry, *Manual of Clinical Microbiology*, Lennette, Spaulding, and Truant, Eds., American Society for Microbiology, Washington, D.C., p. 418 (1974). The minimal inhibitory concentrations (MIC) were determined by applying serial dilutions of the compounds of Formulas I, III, and IV and Virginiamycin M₁ to standard filter paper discs. The concentration of the test compounds ranged from 0.05 μg to 3.0 μg per disc in 20 μl of diluent. The test organism, *Micrococcus luteus*, was inoculated on the surface of an agar based nutrient medium in petri plates and the discs placed on the surface of the medium. The nutrient media consisted of nutrient broth supplemented with 0.2% yeast extract and 1.5% agar. The innoculated plates were incubated for 15 hours at 28° C. and the zones of inhibition determined. The MIC of each compound was determined by the method described in Matsen and Barry, supra. The results are shown in the following table:

TABLE IV

Minimal Inhibitory Concentration

| Compound | IC$_{50}$ (nM) |
|---|---|
| Virginiamycin M$_1$ | 1.5 |
| I | 90.0 |
| III | 250.0 |
| IV | 15.0 |

What is claimed is:

1. A method of treating panic disorder or anxiety disorder in a mammal which comprises administering to said mammal a therapeutically effective amount of a compound of the formula:

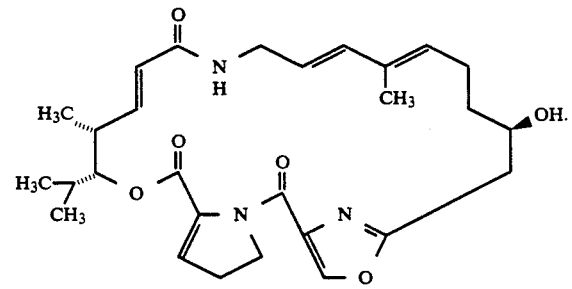

2. A method of treating panic disorder or anxiety disorder in a mammal which comprises administering to said mammal a therapeutically effective amount of a compound of the formula:

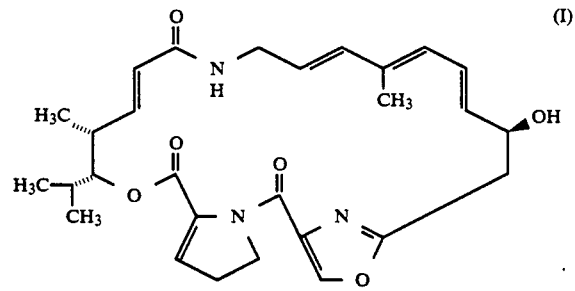

(I)

3. A method of treating panic disorder or anxiety disorder in a mammal which comprises administering to said mammal a therapeutically effective amount of a compound of the formula:

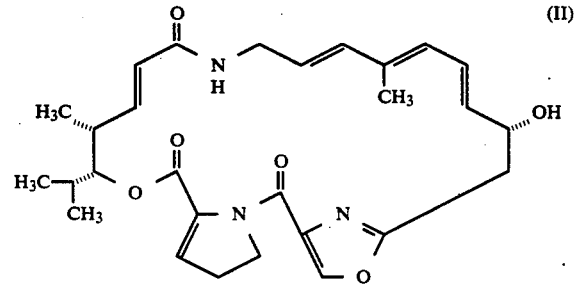

(II)

4. A method of treating panic disorder or anxiety disorder in a mammal which comprises administering to said mammal a therapeutically effective amount of a compound of the formula:

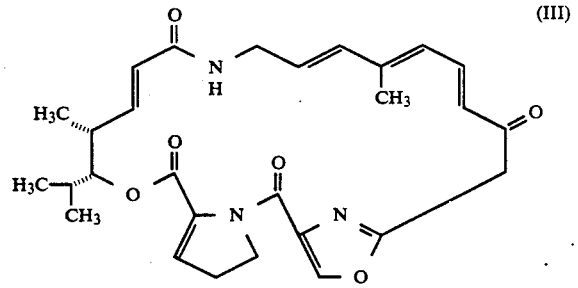

(III)

5. A method of treating panic disorder or anxiety disorder in a mammal which comprises administering to said mammal a therapeutically effective amount of a compound of the formula:

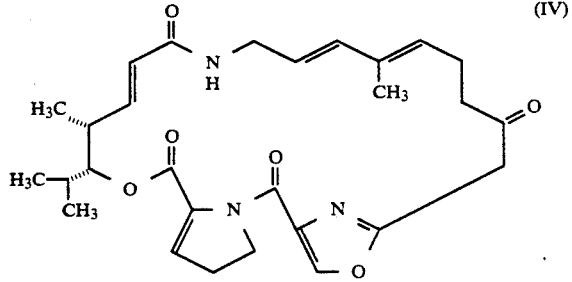

(IV)

6. The method according to claim 1, wherein the therapeutically effective amount of the compound of the Formula is from about 0.005 mg/kg to about 50 mg/kg of body weight, administered to said mammal in a single or divided dose.

7. The method according to claim 4, wherein said mammal is a human.

8. The method according to claim 2, wherein the therapeutically effective amount of the compound of Formula I is from about 0.005 mg/kg to about 50 mg/kg of body weight, administered to said mammal in a single or divided dose.

9. The method according to claim 2 wherein said mammal is a human.

10. The method according to claim 3, wherein the therapeutically effective amount of the compound of Formula II is from about 0.005 mg/kg to about 50 mg/kg of body weight, administered to said mammal in a single or divided dose.

11. The method according to claim 3, wherein said mammal is a human.

12. The method according to claim 4, wherein the therapeutically effective amount of the compound of Formula III is from about 0.005 mg/kg to about 50 mg/kg of body weight, administered to said mammal in a single or divided dose.

13. The method according to claim 4, wherein said mammal is a human.

14. The method according to claim 5, wherein the therapeutically effective amount of the compound of Formula IV is from about 0.005 mg/kg to about 50 mg/kg of body weight, administered to said mammal in a single or divided dose.

15. The method according to claim 5, wherein said mammal is a human.

* * * * *